(12) United States Patent
Kitazaki

(10) Patent No.: US 12,317,212 B2
(45) Date of Patent: May 27, 2025

(54) COMMUNICATION METHOD, RELAY APPARATUS, AND SERVER APPARATUS

(71) Applicant: OLYMPUS CORPORATION, Tokyo (JP)

(72) Inventor: Tomoaki Kitazaki, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 317 days.

(21) Appl. No.: 18/097,590

(22) Filed: Jan. 17, 2023

(65) Prior Publication Data

US 2023/0164724 A1 May 25, 2023

Related U.S. Application Data

(63) Continuation of application No. PCT/JP2020/027952, filed on Jul. 17, 2020.

(51) Int. Cl.
*H04W 56/00* (2009.01)
*H04L 67/12* (2022.01)

(52) U.S. Cl.
CPC .......... *H04W 56/005* (2013.01); *H04L 67/12* (2013.01)

(58) Field of Classification Search
CPC ............................. H04W 56/005; H04L 67/12
See application file for complete search history.

(56) References Cited

U.S. PATENT DOCUMENTS

2019/0158340 A1* 5/2019 Zhang .................. H04B 17/318

FOREIGN PATENT DOCUMENTS

| JP | 2006-343177 A | 12/2006 |
|---|---|---|
| JP | 2009-075736 A | 4/2009 |
| JP | 2019-159448 A | 9/2019 |
| WO | 2018/110047 A1 | 6/2018 |

OTHER PUBLICATIONS

International Preliminary Report on Patentability dated Jan. 17, 2023 and Written Opinion of the International Searching Authority dated Oct. 20, 2020 received in PCT/JP2020/027952.
International Search Report dated Oct. 20, 2020 received in PCT/JP2020/027952.

* cited by examiner

*Primary Examiner* — Samina F Choudhry
(74) *Attorney, Agent, or Firm* — Scully, Scott, Murphy & Presser, P.C.

(57) ABSTRACT

A verification signal transmission unit transmits a verification signal including time information indicating a current time to a server apparatus via a relay apparatus. The verification signal relay unit receives the verification signal from the medical device and transmits the verification signal to the server apparatus. The verification signal reception unit receives the verification signal, and the offset determination unit compares the time information included in the verification signal with a current time on the server apparatus in UTC time and determines whether the medical device includes a UTC offset in the time information. A determination result transmission unit transmits a result of determination related to a UTC offset to the relay apparatus or the medical device. A determination result reception unit receives the result of determination. A registration unit registers information related to the result of determination in a device information recording unit, mapping the information to device identification information identifying the medical device.

14 Claims, 6 Drawing Sheets

FIG.4

| DEVICE ID | UTC OFFSET APPENDING FUNCTION |
|---|---|
| 0001 | YES |
| 0002 | YES |
| 0003 | YES |
| 0004 | NO |
| 0005 | YES |
| ⋮ | ⋮ |
| 0100 | NO |

44

COMMUNICATION METHOD, RELAY APPARATUS, AND SERVER APPARATUS

CROSS-REFERENCE TO RELATED APPLICATIONS

This application is based upon and claims the benefit of priority from the International Application No. PCT/JP2020/027952, filed on Jul. 17, 2020, the entire contents of which are incorporated herein by reference.

BACKGROUND

1. Field of the Disclosure

The present disclosure relates to a technology for communication between facilities in a medical system.

2. Description of the Related Art

To transmit and receive data between medical facilities in different time zones in the related art, local time information of one of the time zones needs to be converted into local time information of the other time zone by adjusting a time difference. In an environment where there is a time difference between a facility A and a facility B within a given medical group, and the facility A maintains a database that manages the examination schedule of the facility B, the facility B retrieves its examination schedule from the facility A by transmitting a schedule acquisition request to the facility A. In this process, the facility A converts local time information included in the schedule acquisition request transmitted from the facility B into local time information of the facility A and searches the database by the local time information as converted.

Patent literature 1 discloses a medical network system provided with a time zone identification means that identifies the time zone to which each of a requesting terminal and an acknowledgment terminal belongs and a due date calculation means that determines time information related to the due date of an examination result report of the medical examination facility where the acknowledgment terminal is installed and determines converted time information derived from converting the time information into a time with reference to the time zone to which the requesting terminal belongs.

[Patent literature 1] JP2009-75736

Universal Time Coordinated (UTC) is used as the world time reference. By using UTC time information mutually for communication between medical facilities in different time zones, the differences in time zones need not be considered. It is therefore desired to build a scheme for efficiently realizing communication that uses UTC time information.

SUMMARY

The present disclosure addresses the issue described above, and a purpose thereof is to provide a technology for realizing communication that uses UTC time information.

An aspect of the present disclosure relates to a communication method in a medical system including a medical device and a relay apparatus provided in a first facility and a server apparatus provided in a second facility, wherein the medical device is configured to: transmit a verification signal including time information indicating a current time to the server apparatus via the relay apparatus, the server apparatus is configured to: receive the verification signal; compare the time information included in the verification signal with a current time on the server apparatus in UTC time; determine whether the medical device includes a UTC offset in the time information, based on a result of comparison; and transmit a result of determination related to a UTC offset to the relay apparatus or the medical device, and the relay apparatus is configured to: receive the result of determination; and register information related to the result of determination in a storage apparatus, mapping the information to device identification information identifying the medical device.

Another aspect of the present disclosure relates to a medical system including a medical device and a relay apparatus provided in a first facility and a server apparatus provided in a second facility, wherein the medical device includes a verification signal transmission unit that transmits a verification signal including time information indicating a current time to the server apparatus. The relay apparatus includes a verification signal relay unit that receives the verification signal from the medical device and transmits the verification signal to the server apparatus. The server apparatus includes: a verification signal reception unit that receives the verification signal; an offset determination unit that compares the time information included in the verification signal with a current time on the server apparatus in UTC time and determines whether the medical device includes a UTC offset in the time information; and a determination result transmission unit that transmits a result of determination related to a UTC offset to the relay apparatus or the medical device. The relay apparatus includes: a determination result reception unit that receives the result of determination; and a registration unit that registers information related to the result of determination in a device information recording unit, mapping the information to device identification information identifying the medical device.

Optional combinations of the aforementioned constituting elements, and implementations of the present disclosure in the form of methods, apparatuses, systems, recording media or mediums, computer programs, etc. may also be practiced as additional modes of the present disclosure.

BRIEF DESCRIPTION OF THE DRAWINGS

Embodiments will now be described, by way of example only, with reference to the accompanying drawings that are meant to be exemplary, not limiting, and wherein like elements are numbered alike in several figures, in which:

FIG. 4 shows an example of a recording status in the device information recording unit;

DETAILED DESCRIPTION

The disclosure will now be described by reference to the preferred embodiments. This does not intend to limit the scope of the present disclosure, but to exemplify the disclosure.

Figure 1:
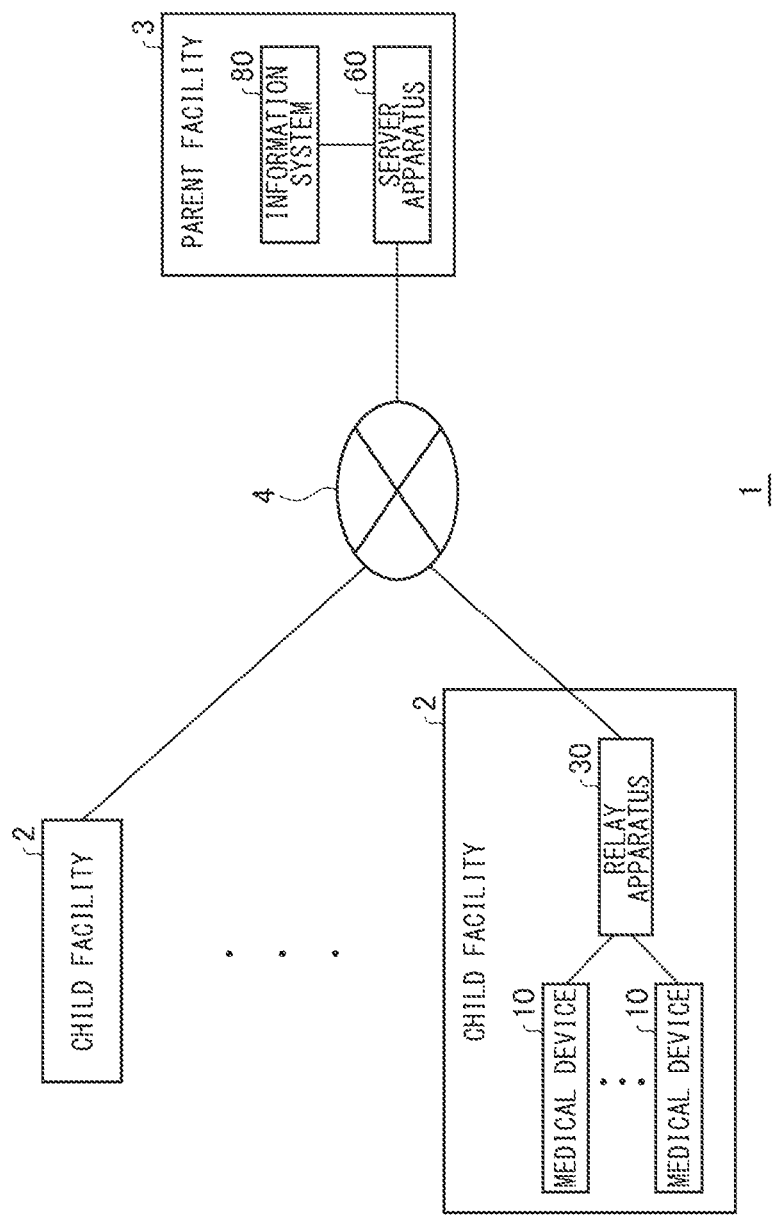
FIG. 1 shows a configuration of a medical system according to an embodiment.

FIG. 1 shows a configuration of a medical system 1 according to an embodiment of the present disclosure. The medical system 1 of the embodiment is configured by connecting a plurality of facilities by a network 4. In this example, one parent facility 3 and a plurality of child facilities 2 are communicably connected by a network 4 such as the Internet.

The parent facility 3 is provided with a server apparatus 60 and an information system 80 and manages medical data in the plurality of child facilities 2. The server apparatus 60 and the information system 80 are installed in the same time zone. The information system 80 may be provided with picture archiving and communication systems, radiology information systems, hospital information systems, etc. and may be provided with functions to manage medical service in each child facility 2. The server apparatus 60 manages data transmission and reception between a medical device 10 in the child facility 2 and the information system 80.

The child facility 2 is a medical institution such as a hospital and is provided with a plurality of medical devices 10 and a relay apparatus 30. The plurality of medical devices 10 and the relay apparatus 30 are connected by an intra-facility local area network (LAN). The medical device 10 is an examination apparatus or a treatment apparatus such as an endoscopic examination apparatus and a radiation therapy apparatus provided in the respective departments in the child facility 2. The medical devices 10 and the relay apparatus 30 in one child facility 2 belong to the same time zone. Therefore, data processing in the child facility 2 is executed by using the local time information of the child facility 2.

In the medical system 1, the child facility 2 and the parent facility 3 are provided in different time zones, and there is a time difference between the local time in the child facility 2 and the local time in the parent facility 3. In the medical system 1, data processing between the child facility 2 and the parent facility 3 is executed based on the UTC time for the purpose of eliminating an impact from the time difference in data processing between facilities.

The UTC time is derived from the local time (a time in a given time zone) and the UTC offset (the time difference between the time zone and UTC (the time at zero longitude)). UTC-8 is the standard time delayed from Universal Time Coordinated by 8 hours (the UTC offset is −8 hours) and is employed as Pacific Standard Time in the United States. For example, (T10:00−8:00) means that the local time is 10:00 and the UTC time is 18:00. Further, UTC-5 is the standard time delayed from Coordinate Universal Time by 5 hours (the UTC offset is −5 hours) and is employed as Eastern Standard Time in the United States. For example, (T13:00−5:00) means that the local time is 13:00 and the UTC time is 18:00. In other words, (T10:00−8:00) in UTC-8 and (T13:00−5:00) in UTC-5 mean the same UTC time (18:00). In the medical system 1, data processing between facilities is executed by using the UTC time.

Data processing between facilities in the medical system 1 actually means data processing between the medical device 10 in the child facility 2 and the information system 80 in the parent facility 3. That the server apparatus 60 and the information system 80 in the parent facility 3 have the function to handle UTC time is a prerequisite, but the medical devices 10 in the child facility 2 are available in various types so that some types can only handle local time. The medical device 10 not having the function to handle UTC time cannot append a UTC offset to the time information included in transmitted data. This is addressed by this embodiment by configuring the relay apparatus 30 provided with the gateway function to have the function to append a UTC offset to the time information for data transmitted from the medical device 10 not having the function to handle UTC time.

Figure 2:
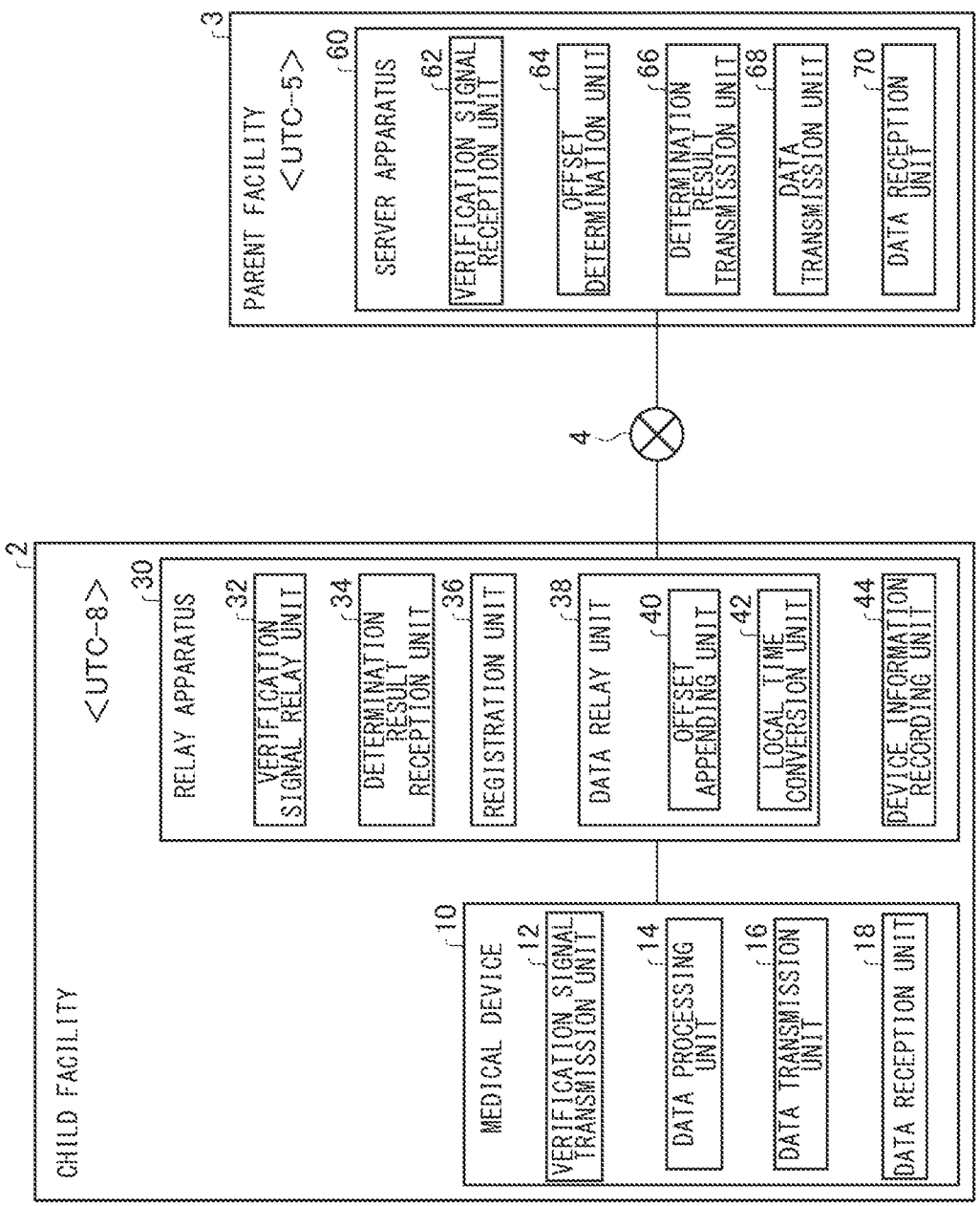
FIG. 2 shows functional blocks of the medical device, the relay apparatus, and the server apparatus.

FIG. 2 shows functional blocks of the medical device 10, the relay apparatus 30, and the server apparatus 60. Each of the medical device 10, the relay apparatus 30, and the server apparatus 60 is provided with a processor that includes hardware. In the embodiment, it is assumed that the child facility 2 uses UTC-8 as the standard time and the parent facility 3 uses UTC-5 as the standard time.

The medical device 10 is provided with a verification signal transmission unit 12, a data processing unit 14, a data transmission unit 16, and a data reception unit 18. The relay apparatus 30 is provided with a verification signal relay unit 32, a determination result reception unit 34, a registration unit 36, a data relay unit 38, and a device information recording unit 44. The data relay unit 38 includes an offset appending unit 40 and a local time conversion unit 42. The server apparatus 60 is provided with a verification signal reception unit 62, an offset determination unit 64, a determination result transmission unit 66, a data transmission unit 68, and a data reception unit 70.

The features shown in FIG. 2 are implemented in hardware such as an arbitrary processor, a memory, an auxiliary storage apparatus, or other LSI's and in software such as a program loaded into a memory. The figure depicts functional blocks implemented by the cooperation of these elements. Therefore, it will be understood by those skilled in the art that the functional blocks may be implemented in a variety of manners by hardware only, software only, or by a combination of hardware and software. The device information recording unit 44 may be a storage or a storage apparatus.

When the new medical device 10 is connected to the intra-facility LAN in the child facility 2, a process of verifying whether the medical device 10 has the function to handle UTC time is performed. As described above, the child facility 2 uses UTC-8 as the standard time, and the parent facility 3 uses UTC-5 as the standard time.

Figure 3:
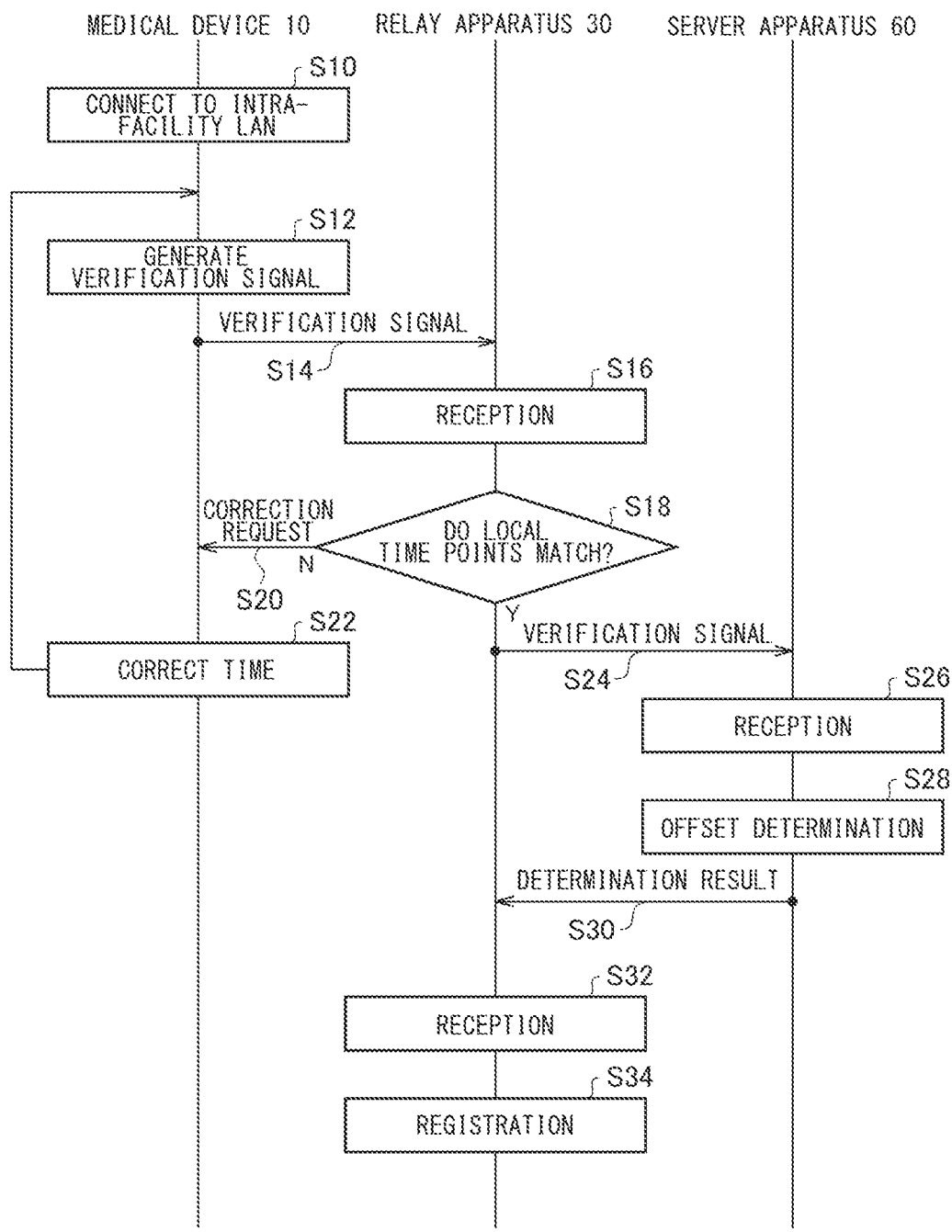
FIG. 3 is a sequence chart showing a step of verifying whether the function to handle UTC time is provided.

FIG. 3 is a sequence chart showing a step of verifying whether the medical device 10 has the function to handle UTC time. When the new medical device 10 is connected to the intra-facility LAN (S10), the verification signal transmission unit 12 generates a verification signal verifying whether the function to handle UTC time is included and including time information indicating the current time (S12). The verification signal transmission unit 12 transmits the verification signal to the server apparatus 60 via the relay apparatus 30 (S14). It will be assumed that the medical device 10 is connected at the local time 12:00 in the child facility 2. The relay apparatus 30 includes the gateway function, and the verification signal relay unit 32 receives the verification signal temporarily (S16).

The verification signal relay unit 32 compares the current time indicated by the time information included in the verification signal with the current time on the relay apparatus 30 in terms of local time (S18). The relay apparatus 30 is provided with accurate time information by connecting to the NTP server. When the current time included in the verification signal and the current time on the relay apparatus 30 do not match in terms of local time (N in S18), the verification signal relay unit 32 transmits a request for correction of the time to the medical device 10 (S20). When the medical device 10 receives the request for correction, the medical device 10 corrects the current time (S22), generates a verification signal including time information indicating the current time (S12), and transmits the verification signal to the server apparatus 60 via the relay apparatus 30 (S14). When the verification signal relay unit 32 receives the verification signal temporarily (S16) and determines that the current time included in the verification signal and the current time on the relay apparatus 30 match in terms of local time (Y in S18), the verification signal relay unit 32 transmits the verification signal to the server apparatus 60 (S24).

In the case the medical device 10 has the function to handle UTC time, the verification signal transmission unit 12 includes time information indicating the current time in the form of (T12:00−8:00) in the verification signal in S12. 12:00 represents the local time, and −8:00 represents the UTC offset. In the case the medical device 10 does not have the function to handle UTC time, on the other hand, the verification signal transmission unit 12 includes time information indicating the current time in the form of (T12:00) in the verification signal in S12. In essence, the time information indicating the current time includes a local time but does not include a UTC offset, provided that the medical device 10 does not have the function to handle UTC time.

In the server apparatus 60, the verification signal reception unit 62 receives the verification signal from the medical device 10 (S26). The server apparatus 60 and the information system 80 in the parent facility 3 are provided with accurate time information by connecting to the NTP server. The offset determination unit 64 in the server apparatus 60 compares the time information included in the verification signal with the current time on the server apparatus 60 in terms of UTC time and determines whether the medical device 10 includes a UTC offset in the time information based on the result of comparison (S28). In this case, the time information for the current time on the server apparatus 60 is (T15:00−5:00), and the UTC time is 20:00.

When the time information included in the verification signal is (T12:00−8:00) and includes a UTC offset, the offset determination unit 64 calculates the UTC time for the current time included in the verification signal as being 20:00. In this case, the both UTC times (both points of time in UTC time) match so that the offset determination unit 64 determines that the medical device 10 includes a UTC offset in the time information. The offset determination unit 64 may allow for a communication delay from the medical device 10 to the server apparatus 60 and determine that the both UTC times match even if there is a time lag within a predetermined time (e.g., 15 minutes). It will be noted that 15 minutes is the minimum time difference in standard time in the world.

When the time information included in the verification signal is (T12:00) and does not include a UTC offset, the offset determination unit 64 cannot calculate the UTC time from the time information included in the verification signal, and the time information included in the verification signal does not match the UTC time in the server apparatus 60. Therefore, the offset determination unit 64 determines that the medical device 10 does not include a UTC offset in the time information.

The determination result transmission unit 66 transmits the result of determination related to a UTC offset to the relay apparatus 30 or the medical device 10 (S30). In the child facility 2, the result of determination transmitted to the medical device 10 is received by the relay apparatus 30 before arriving at the medical device 10. Therefore, the result of determination is ensured to be received by the relay apparatus 30 whichever of the relay apparatus 30 and the medical device 10 is the destination designated by the determination result transmission unit 66.

In the relay apparatus 30, the determination result reception unit 34 receives the result of determination related to a UTC offset (S32). The registration unit 36 registers information related to the result of determination in the device information recording unit 44, mapping the information to device identification information (device ID) for identifying the medical device 10 (S34).

FIG. 4 shows an example of a recording status in the device information recording unit 44. The device information recording unit 44 records information related to the result of determination on a UTC offset, mapping the information to the device ID of the medical device 10. The information related to the result of determination is information indicating whether the medical device 10 has the function to append a UTC offset to the time information, but may be different information (e.g., information indicating whether UTC time can be handled). In the example shown in FIG. 4, it is recorded that the medical devices 10 with the devices ID "0004" and "0100" do not have the function to append a UTC offset to the time information.

In the sequence chart shown in FIG. 3, the result of determination transmitted from the server apparatus 60 is not transferred to the medical device 10, but may be transferred to the medical device 10. The medical device 10 can confirm communication with the server apparatus 60 by receiving the result of determination.

The process shown in FIG. 3 may be executed once when the new medical device 10 is connected to the intra-facility LAN, and the information indicating whether the function to append a UTC offset is provided may be registered in the device information recording unit 44. There are cases where the medical device 10 did not have the function to handle UTC when it first connected to the intra-facility LAN, but may have acquired the function to handle UTC through a subsequent software update. Therefore, the process shown in FIG. 3 may be executed automatically when the medical device 10 is powered on. After the information indicating whether the function to append a UTC offset is provided is registered in the device information recording unit 44, the medical device 10 transmits and receives medical data to and from the information system 80.

Figure 5:
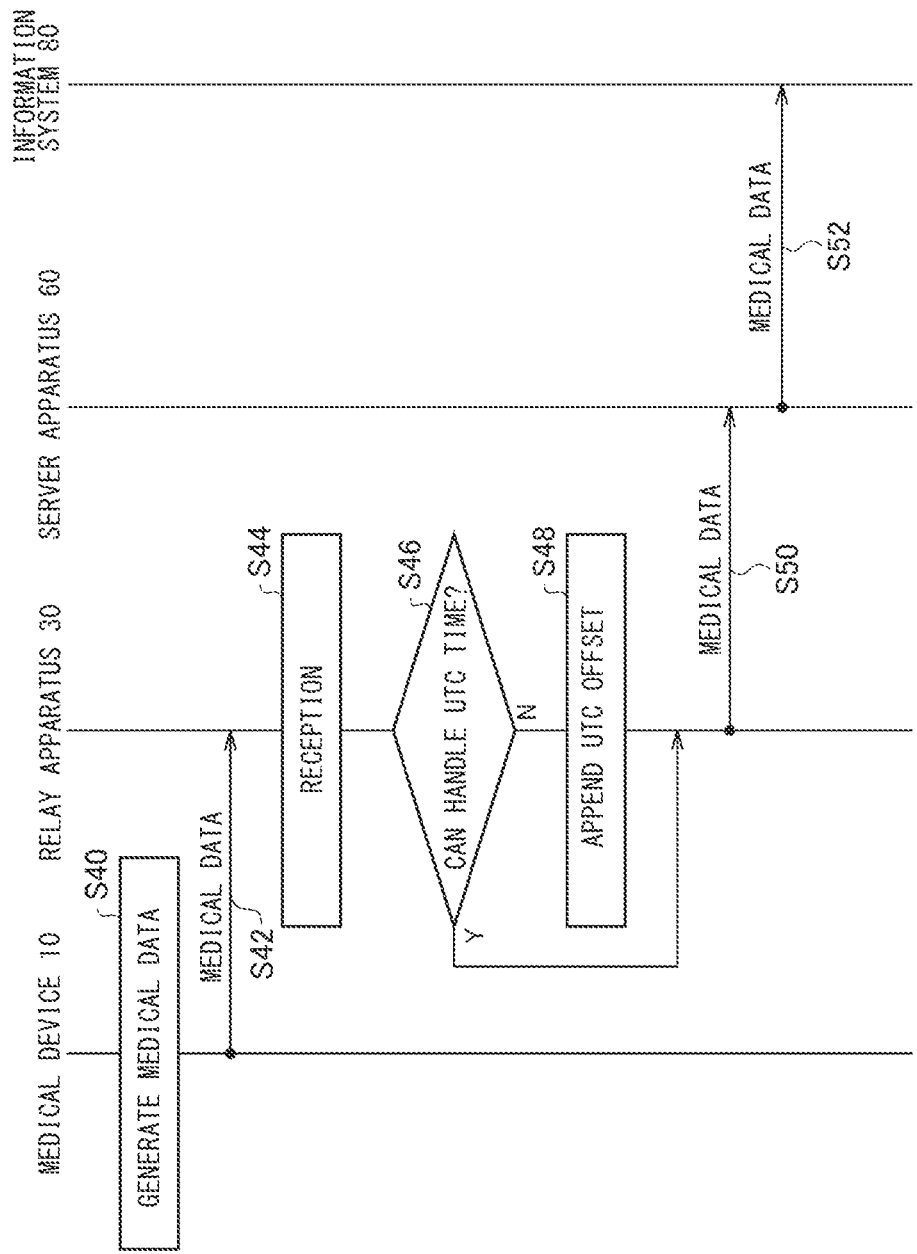
FIG. 5 is a sequence chart showing a process in which the medical device transmits medical data.

FIG. 5 is a sequence chart showing a process in which the medical device 10 transmits medical data. When medical data that should be transmitted to the information system 80 arises in the medical device 10, the data processing unit 14 generates the medical data including time information (S40), and the data transmission unit 16 transmits the medical data to the information system 80 via the server apparatus 60 (S42). The transmitted medical data is received by the data relay unit 38 in the relay apparatus 30 temporarily (S44).

When the data relay unit 38 receives the medical data transmitted from the medical device 10, the data relay unit 38 determines whether to append a UTC offset to the time information in the medical data, based on the information mapped to the device ID of the medical device 10 in the device information recording unit 44 (S46). When the information mapped to the device ID indicates that the medical device 10 does not have the function to append a UTC offset in the device information recording unit 44 (N in S46), the offset appending unit 40 appends a UTC offset to the time information in the medical data (S48).

When the medical device 10 does not have the function to append a UTC offset, the time information in the medical data includes a local time, but does not include a UTC offset. By using the offset appending unit 40 to append a UTC offset to the time information in the medical data, the medical data transmitted from the medical device 10 will be handled in the information system 80 in UTC time, which is Coordinate Universal Time.

When the information mapped to the device ID indicates that the medical device 10 has the function to append a UTC offset in the device information recording unit 44 (Y in S46), a UTC offset is appended to the time information in the medical data so that the offset appending unit 40 does not append a UTC offset to the time information in the medical data.

The data relay unit 38 transmits the medical data including the time information to which the UTC offset is appended to the server apparatus 60 (S50). In the server apparatus 60, the data reception unit 70 receives the medical data transmitted from the medical device 10, and the data transmission unit 68 transfers the medical data to the information system 80 (S52). The information system 80 derives the UTC time from the time information in the medical data and executes a process using the UTC time.

For example, a description will be given of a case where the medical device 10 requests a list of examinations that start at 10:00 a.m. local time in the child facility 2 from the information system 80. In this case, the start time 10:00 of the examination is represented by time information (T10:00-8:00), and the medical data (examination list request) transmitted from the data relay unit 38 to the information system 80 via the server apparatus 60 includes the time information (10:00-8:00).

The information system 80 has a database of examination schedules in the respective child facilities 2 and manages the start time of the examination in UTC time. When the information system 80 acquires the examination list request, which includes the time information (T10:00-8:00) as the examination start time, from the child facility 2, the information system 80 searches the database for the examination for which the start time in UTC time is 18:00. More specifically, the information system 80 searches the database for data for the examination (examination data) for which the start time (T13:00-5:00) is set and transmits the data to the medical device 10.

Figure 6:
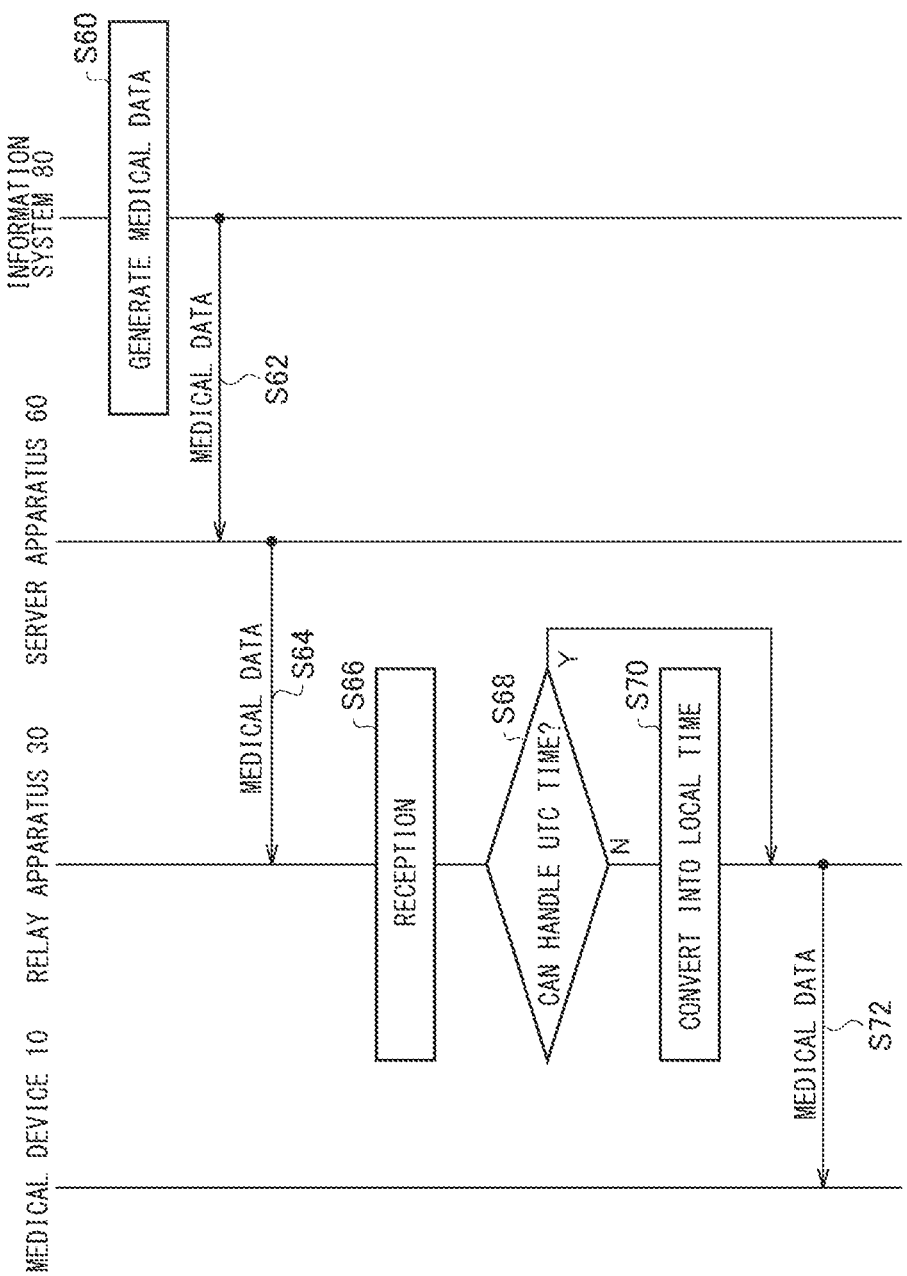
FIG. 6 is a sequence chart showing a process in which the information system transmits medical data.

FIG. 6 is a sequence chart showing a process in which the information system 80 transmits medical data. When medical data that should be transmitted to the medical device 10 arises in the information system 80, the information system 80 generates the medical data including time information with a UTC offset (S60) and transmits the medical data to the medical device 10 via the server apparatus 60 (S62). It is assumed that the medical data is examination data for which the start time (T13:00-5:00) is set. In the server apparatus 60, the data reception unit 70 receives the medical data including the time information with the UTC offset temporarily, and the data transmission unit 68 transmits the medical data to the medical device 10 (S64). The transmitted medical data is temporarily received by the data relay unit 38 in the relay apparatus 30 (S66).

When the data relay unit 38 receives the medical data destined to the medical device 10, the data relay unit 38 determines whether to convert the time information in the medical data into a local time in the child facility 2, based on the information mapped to the device ID of the destination medical device 10 in the device information recording unit 44 (S68). When the information mapped to the device ID indicates that the medical device 10 does not have the function to append a UTC offset in the device information recording unit 44 (N in S68), the local time conversion unit 42 converts the time information in the medical data into a local time (S70) and transmits the medical data to the medical device 10 (S72).

When the medical device 10 does not have the function to append a UTC offset, the medical device 10 cannot process the UTC offset included in the time information in the medical data. In other words, the medical device 10 cannot convert the time information in the medical data into a local time in the child facility 2. By using the local time conversion unit 42 to convert the time information into a local time in the child facility 2, therefore, the medical data transmitted from the information system 80 will be handled in the medical device 10 in local time, which is the standard time in the child facility 2.

When the information mapped to the device ID indicates that the medical device 10 has the function to append a UTC offset in the device information recording unit 44 (Y in S68), on the other hand, the medical device 10 can convert the time information into a local time so that the local time conversion unit 42 need not convert the time information into a local time.

Described above is an explanation based on an embodiment. The embodiment is intended to be illustrative only and it will be understood by those skilled in the art that various modifications to combinations of constituting elements and processes are possible and that such modifications are also within the scope of the present disclosure. For example, the offset determination unit 64 compares the time information included in the verification signal with the current time on the server apparatus 60 in terms of UTC time in S28 shown in FIG. 3. Alternatively, a comparative determination may be executed in the relay apparatus 30. In this case, when the server apparatus 60 receives the verification signal, the server apparatus 60 appends UTC time information indicating the current time on the parent facility 3 to the verification signal and returns the resultant verification signal to the relay apparatus 30. The relay apparatus 30 may execute the determination function of the offset determination unit 64 and determine whether the medical device 10 includes a UTC offset in the time information.

What is claimed is:

1. A communication method in a medical system including a medical device and a relay apparatus provided in a first facility and a server apparatus provided in a second facility, wherein the method comprising:

the medical device:
transmits a verification signal including time information indicating a current time to the server apparatus via the relay apparatus;

the server apparatus:
receives the verification signal;
compares the time information included in the verification signal with a current time on the server apparatus in Universal Time Coordinated (UTC) time;
determines whether the medical device includes a UTC offset in the time information, based on a result of comparison; and
transmits a result of determination related to the UTC offset to the relay apparatus or the medical device, and the relay apparatus:
receives the result of determination; and
registers information related to the result of determination in a storage apparatus, mapping the information to device identification information identifying the medical device.

2. The communication method according to claim 1, wherein the medical device:
transmits first data including time information to the relay apparatus,
the relay apparatus:
receives the first data from the medical device; and
determines whether to append a UTC offset to the time information in the first data, based on the information mapped to the device identification information of the medical device in the storage apparatus.

3. The communication method according to claim 2, wherein
when the mapped information indicates that the medical device does not have a function to append a UTC offset, the relay apparatus appends the UTC offset to the time information in the first data.

4. The communication method according to claim 1, wherein
the server apparatus:
transmits second data including time information with a UTC offset to the medical device, and
the relay apparatus:
receives the second data from the server apparatus; and
determines whether to convert the time information in the second data into a local time in the first facility, based on the information mapped to device identification information of the medical device in the storage apparatus.

5. The communication method according to claim 4, wherein
when the mapped information indicates that the medical device does not have a function to append a UTC offset, the relay apparatus converts the time information in the second data into the local time in the first facility.

6. The communication method according to claim 2, wherein
the server apparatus:
transmits second data including time information with a UTC offset to the medical device, and
the relay apparatus:
receives the second data from the server apparatus; and
determines whether to convert the time information in the second data into a local time in the first facility, based on the information mapped to device identification information of the medical device in the storage apparatus.

7. The communication method according to claim 3, wherein
the server apparatus:
transmits second data including time information with a UTC offset to the medical device, and
the relay apparatus:
receives the second data from the server apparatus; and
determines whether to convert the time information in the second data into a local time in the first facility, based on the information mapped to device identification information of the medical device in the storage apparatus.

8. The communication method according to claim 6, wherein
when the mapped information indicates that the medical device does not have a function to append a UTC offset, the relay apparatus converts the time information in the second data into the local time in the first facility.

9. A relay apparatus comprising:
a processor including hardware, wherein the processor is configured to:
receive a verification signal transmitted by a medical device to a server apparatus and including time information indicating a current time;
transmit the verification signal to the server apparatus;
receive from the server apparatus a result of determination indicating whether the medical device includes a Universal Time Coordinated (UTC) offset in the time information; and
register information related to the result of determination in a storage apparatus, mapping the information to device identification information identifying the medical device.

10. The relay apparatus according to claim 9, wherein the processor is configured to:
receive first data transmitted by the medical device to the server apparatus and including time information; and
determine whether to append a UTC offset to the time information in the first data, based on the information mapped to the device identification information of the medical device in the storage apparatus.

11. The relay apparatus according to claim 10, wherein the processor is configured to:
when the mapped information indicates that the medical device does not have a function to append a UTC offset, append a UTC offset to the time information in the first data.

12. The relay apparatus according to claim 9, wherein the processor is configured to:
receive second data transmitted by the server apparatus to the medical device and including time information with a UTC offset; and
determine whether to convert the time information in the second data into a local time in the first facility, based on the information mapped to device identification information of the medical device in the storage apparatus.

13. The relay apparatus according to claim 12, wherein the processor is configured to:
when the mapped information indicates that the medical device does not have a function to append a UTC offset, convert the time information in the second data into the local time in the first facility.

14. A server apparatus comprising:
a processor including hardware, wherein the processor is configured to:
receive a verification signal including time information indicating a current time on a medical device;
compare the time information included in the verification signal with a current time on the server apparatus in Universal Time Coordinated (UTC) time;
determine whether the medical device includes a UTC offset in the time information, based on a result of comparison; and
transmit a result of determination related to a UTC offset to the relay apparatus or the medical apparatus.

* * * * *